(12) United States Patent
Bagherifard Sharabiani et al.

(10) Patent No.: US 11,566,126 B2
(45) Date of Patent: Jan. 31, 2023

(54) POLYMERIC COMPOSITIONS FOR ENHANCING GRIP

(71) Applicants: Mina Bagherifard Sharabiani, Karaj (IR); Zeinab Sadat Ziabakhsh, Tehran (IR); Ali Pourjavadi, Tehran (IR)

(72) Inventors: Mina Bagherifard Sharabiani, Karaj (IR); Zeinab Sadat Ziabakhsh, Tehran (IR); Ali Pourjavadi, Tehran (IR)

(73) Assignee: SHARIF UNIVERSITY OF TECHNOLOGY, Tehran (IR)

( * ) Notice: Subject to any disclaimer, the term of this patent is extended or adjusted under 35 U.S.C. 154(b) by 157 days.

(21) Appl. No.: 17/207,633

(22) Filed: Mar. 20, 2021

(65) Prior Publication Data

US 2021/0206956 A1    Jul. 8, 2021

Related U.S. Application Data

(60) Provisional application No. 63/051,394, filed on Jul. 14, 2020.

(51) Int. Cl.
| | |
|---|---|
| C08L 31/04 | (2006.01) |
| C08K 5/098 | (2006.01) |
| A61K 8/19 | (2006.01) |
| A61K 8/81 | (2006.01) |
| A61K 8/04 | (2006.01) |
| F26B 5/00 | (2006.01) |
| A61Q 19/00 | (2006.01) |
| A61Q 90/00 | (2009.01) |
| C08K 3/26 | (2006.01) |

(52) U.S. Cl.
CPC .............. *C08L 31/04* (2013.01); *A61K 8/042* (2013.01); *A61K 8/19* (2013.01); *A61K 8/8135* (2013.01); *A61Q 19/00* (2013.01); *A61Q 90/00* (2013.01); *C08K 5/098* (2013.01); *F26B 5/005* (2013.01); *C08K 2003/267* (2013.01); *C08L 2205/03* (2013.01)

(58) Field of Classification Search
None
See application file for complete search history.

(56) References Cited

U.S. PATENT DOCUMENTS

| | | | | |
|---|---|---|---|---|
| 9,782,887 | B2 * | 10/2017 | Jaskolski | ............... A61Q 15/00 |
| 2001/0046475 | A1 * | 11/2001 | Barth | ....................... A61K 8/24 |
| | | | | 424/49 |
| 2015/0147468 | A1 * | 5/2015 | Diehn | .................. C09D 105/08 |
| | | | | 524/29 |

* cited by examiner

*Primary Examiner* — David J Buttner
(74) *Attorney, Agent, or Firm* — Bajwa IP Law Firm; Haris Zaheer Bajwa (57) ABSTRACT

A polymeric composition for enhancing grip, including a modified solvent phase and a solid phase dispersed within the modified solvent phase. The modified solvent phase may include calcium-based gel, including calcium acetate particles partially dissolved in an alcoholic solution. The solid phase also includes a polymeric matrix and a plurality of desiccant particles encompassed by the polymeric matrix. The polymeric matrix includes polyvinyl acetate (PVAc) and a thickener.

20 Claims, 8 Drawing Sheets

POLYMERIC COMPOSITIONS FOR ENHANCING GRIP

CROSS-REFERENCE TO RELATED APPLICATION

This application claims the benefit of priority from U.S. Provisional Patent Application Ser. No. 63/051,394, filed on Jul. 14, 2020, and entitled "SUSPENSION CHALK," which is incorporated herein by reference in its entirety.

TECHNICAL FIELD

The present disclosure generally relates to grip-enhancing compositions, particularly to polymeric compositions for enhancing grip, and more particularly to polymeric suspension or gel to enhance grip.

BACKGROUND

While clinging on to objects is required in many sports like climbing, tight gripping often becomes challenging in the presence of moisture, which reduces the friction between hands and the objects. In some sports where skin is in contact with another surface, friction between the body and the surface is essential, and therefore, moist skin may reduce training quality. Some typical approaches for reducing sweat are wearing gloves or some surface treatments like chalk, which facilitates a secure grip. However, gloves may not be appropriate in some sports because the typical thickness of gloves restricts hand movement and limits the sense of touch. Also, the gloves may be taken off during the training.

Solid chalk has been used for many years. However, small particles of the solid chalk may suspend in the air and may cause health problems, like respiratory diseases in the long run due to inhaling small particles of chalk dust; therefore, solid chalk may not be appropriate for consistent indoor use. In order to overcome the problems of solid chalk, liquid chalks have been developed containing chalk, alcohol, thickener, and essential oils. However, harmful organic solvents like benzyl alcohol and toxic stabilizers are used in conventional liquid chalk.

Hence, there is a need for efficient grip-enhancing compositions, including a stabilizer matrix that surrounds the chalk and makes an interface between the chalk and alcohol. Also, there is a need for a simple and cost-effective method for producing a safe and environmentally friendly grip-enhancing composition.

SUMMARY

This summary is intended to provide an overview of the subject matter of the present disclosure and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary polymeric composition for enhancing grip, including a modified solvent phase and a solid phase dispersed within the modified solvent phase. In an exemplary embodiment, the modified solvent phase may include a calcium-based gel. In an exemplary embodiment, the calcium-based gel may include calcium acetate particles partially dissolved in an alcoholic solution. In an exemplary embodiment, the solid phase may include a polymeric matrix and a plurality of desiccant particles encompassed by the polymeric matrix.

In an exemplary embodiment, the polymeric matrix may include polyvinyl acetate (PVAc) and a thickener. In an exemplary embodiment, the PVAc may have a concentration between about 2 g/ml and about 5 g/ml of exemplary polymeric composition. In an exemplary embodiment, exemplary polymeric composition may include the calcium acetate particles with a concentration between about 1% and about 4% of exemplary polymeric composition by weight. In an exemplary embodiment, the calcium-based gel may include at least one of nanoparticles and microparticles.

In an exemplary embodiment, the alcoholic solution may include alcohol dissolved in water with a concentration of the alcohol between about 60% and about 99% by volume. In an exemplary embodiment, the alcohol may include at least one of isopropyl alcohol and ethanol. In an exemplary embodiment, the alcoholic solution may include a volume ratio between about 60% and about 94% of volume of exemplary polymeric composition. In an exemplary embodiment, the plurality of desiccant particles may include at least one of magnesium carbonate ($MgCO_3$), magnesium hydrogen carbonate ($Mg(HCO_3)_2$), calcium carbonate ($CaCO_3$). In an exemplary embodiment, the plurality of desiccant particles may have a concentration between about 3 g/ml and about 15 g/ml of exemplary polymeric composition.

In an exemplary embodiment, the thickener may include at least one of hydroxypropyl methylcellulose (HPMC), colophony resin (rosin), hydroxypropyl cellulose, styrax benzoin gum, hydroxyl ethyl cellulose, and wax. In an exemplary embodiment, the thickener may have a concentration between about 1 g/ml and about 3 g/ml of exemplary polymeric composition. In an exemplary embodiment, exemplary polymeric composition may have a particle size between about 70 nm and about 400 µm. In an exemplary embodiment, exemplary polymeric composition may have a suspension formulation or a gel formulation.

In an exemplary embodiment, exemplary polymeric composition may further include a gelling agent. In an exemplary embodiment, the gelling agent may include a carbomer and a proton acceptor. In an exemplary embodiment, the carbomer may have a concentration between about 0.06 g/ml and about 3 g/ml of exemplary polymeric composition. In an exemplary embodiment, the carbomer may include polyacrylic acid. In an exemplary embodiment, the proton acceptor may have a volume ratio between about 0.0001% and about 0.1% of volume of exemplary polymeric composition. In an exemplary embodiment, the proton acceptor may include a trialkanol amine. In an exemplary embodiment, the trialkanol amine may include an alkyl group with a carbon number up to 5.

In another general aspect, the present disclosure describes an exemplary method for producing an exemplary polymeric composition for enhancing grip. In an exemplary embodiment, an exemplary method may include forming a first mixture by dissolving polyvinyl acetate (PVAc) and a thickener in an alcoholic solution; forming a second mixture by adding a plurality of desiccant particles to the first mixture; and producing exemplary polymeric composition containing calcium-based gel by dropwise adding a saturated calcium solution to the second mixture.

In an exemplary embodiment, the saturated calcium solution may include calcium acetate particles with a concentration between about 5% and about 20% of the saturated calcium solution by weight. In an exemplary embodiment, mixing the saturated calcium solution with the second mixture may include mixing the saturated calcium solution with the second mixture with a volume ratio of the saturated calcium solution to the second mixture between about 15% and about 30%.

BRIEF DESCRIPTION OF THE DRAWINGS

The drawing figures depict one or more implementations in accordance with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well-known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown but is to be accorded the widest possible scope consistent with the principles and features disclosed herein.

The present disclosure describes an exemplary polymeric composition as liquid chalk to rectify health risks related to solid chalk and improve chalk adhesion to skin. An exemplary polymeric composition may improve an individual's ability to grip an object, especially a sports object such as sport climbing holds or yoga mats, by absorbing sweat and increasing friction between an object and skin. An exemplary polymeric composition may include desiccant particles, which may be suspended in an alcoholic solvent using a polymeric matrix and a calcium-based gel. An exemplary polymeric composition may be applied to hands, feet, or sport objects for better gripping.

Figure 1:
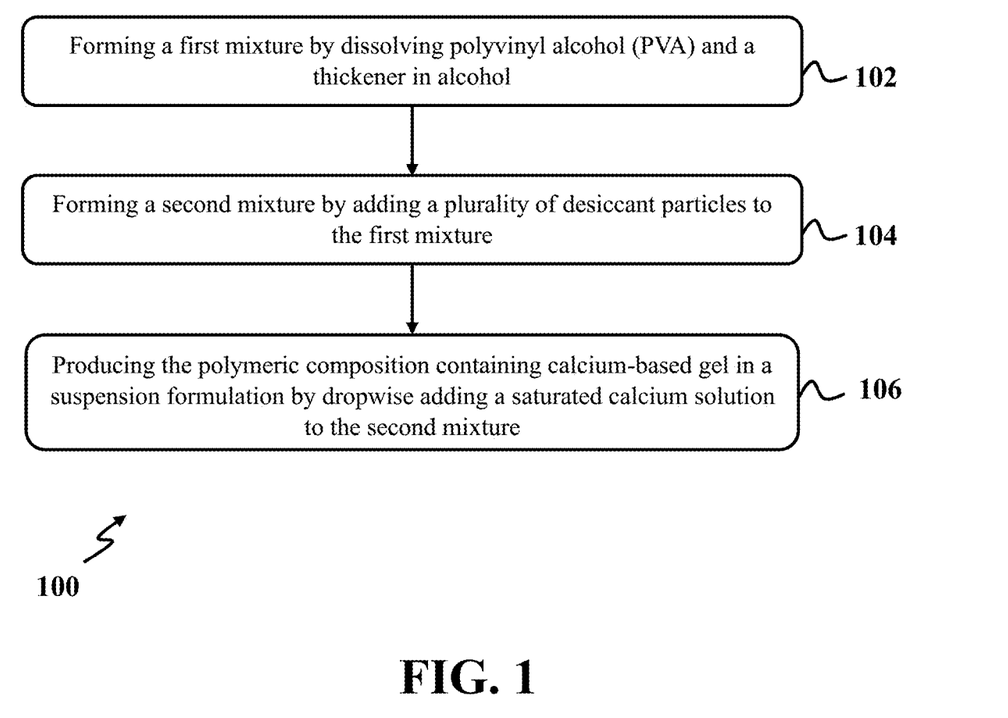
FIG. 1 illustrates a flowchart of an exemplary method for producing an exemplary polymeric composition for enhancing grip, consistent with one or more exemplary embodiments of the present disclosure.
Figure 2:
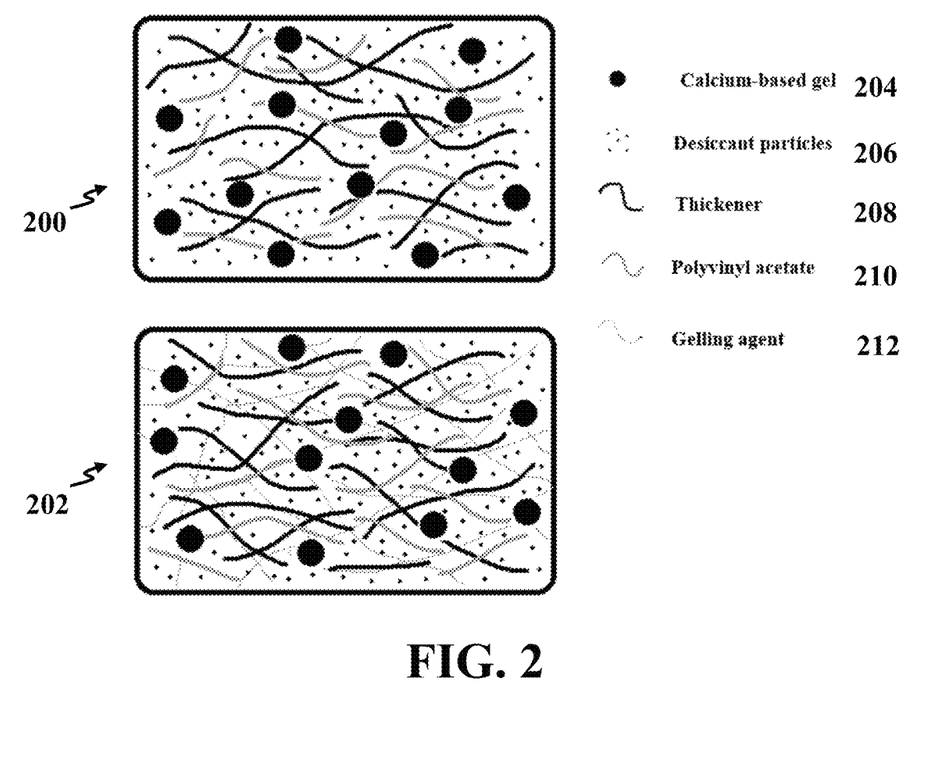
FIG. 2 illustrates a schematic view of an exemplary polymeric composition for enhancing grip, consistent with one or more exemplary embodiments of the present disclosure.

In an exemplary embodiment, exemplary polymeric composition may be produced in a suspension formulation or a gel formulation. FIG. 1 illustrates a flowchart of an exemplary method 100 for producing an exemplary polymeric composition in a suspension formulation for enhancing grip, consistent with one or more exemplary embodiments of the present disclosure. FIG. 2 illustrates a schematic view of exemplary polymeric compositions for enhancing grip in a suspension formulation 200 and a gel formulation 202, consistent with one or more exemplary embodiments of the present disclosure. Exemplary polymeric compositions 200 and 202 may be produced utilizing a process similar to exemplary method 100 of FIG. 1.

Referring to FIG. 1, an exemplary method 100 may include forming a first mixture by dissolving polyvinyl acetate (PVAc) and a thickener in an alcoholic solution (step 102), forming a second mixture by adding a plurality of desiccant particles to the first mixture (step 104), and producing exemplary polymeric composition containing calcium-based gel in a suspension formulation by dropwise adding a saturated calcium solution to the second mixture (step 106).

In further detail with respect to step 102, in an exemplary embodiment, forming a first mixture may include completely dissolving PVAc 210 and a thickener 208 in an alcoholic solution until obtaining a transparent solution as the first mixture. In an exemplary embodiment, dissolving PVAc 210 and thickener 208 in the alcoholic solution may include mixing PVAc 210 and thickener 208 with the alcoholic solution at a temperature between about 70° C. and about 90° C. In an exemplary embodiment, mixing PVAc 210 and thickener 208 with the alcoholic solution may include mixing PVAc 210 and thickener 208 with the alcoholic solution using a stirrer at speed between about 400 revolutions per minute (rpm) and about 800 rpm.

In an exemplary embodiment, the alcoholic solution may include alcohol dissolved in water with a concentration of the alcohol between about 60% and about 99% by volume. In an exemplary embodiment, the alcoholic solution may include alcohol dissolved in water with a concentration of the alcohol of about 76% by volume. In an exemplary embodiment, the alcohol may include alcohol with a small carbon chain up to three (3) carbons. In an exemplary embodiment, the alcohol may include at least one of isopropyl alcohol and ethanol. In an exemplary embodiment, the alcoholic solution may include a volume ratio between about 60% and about 94% of volume of exemplary polymeric composition.

In an exemplary embodiment, the first mixture may be converted to a polymeric matrix in exemplary polymeric composition 200 and 202. In an exemplary embodiment, the polymeric matrix may include thickener 208 and PVAc 210. In an exemplary embodiment, PVAc 210 may have a concentration between about 2 g/ml and about 5 g/ml of exemplary polymeric composition. In an exemplary embodiment, thickener 208 may include a cellulosic substance. In an exemplary embodiment, thickener 208 may include at least one of hydroxypropyl methylcellulose (HPMC), colophony resin (rosin), hydroxypropyl cellulose, styrax benzoin gum, hydroxyl ethyl cellulose, and wax. In an exemplary embodiment, thickener 208 may have a concentration between about 1 g/ml and about 3 g/ml of an exemplary polymeric composition.

In further detail with respect to step 104, in an exemplary embodiment, forming a second mixture may include adding plurality of desiccant particles 206 to the first mixture. In an exemplary embodiment, adding plurality of desiccant particles 206 to the first mixture may include gradually mixing plurality of desiccant particles 206 with the first mixture at a temperature between about 70° C. and about 90° C. using a stirrer with speed between about 400 rpm and about 800 rpm.

In an exemplary embodiment, plurality of desiccant particles 206 may include at least one of magnesium carbonate ($MgCO_3$), magnesium hydrogen carbonate ($Mg(HCO_3)_2$), calcium carbonate ($CaCO_3$). In an exemplary embodiment, plurality of desiccant particles 206 may have a concentration between about 3 g/ml and about 15 g/ml of exemplary polymeric composition. In an exemplary embodiment, plurality of desiccant particles 206 may include neutral drying powders for increasing friction.

In further detail with respect to step 106, in an exemplary embodiment, producing exemplary polymeric composition containing calcium-based gel in a suspension formulation may include dropwise adding a saturated calcium solution to the second mixture. In an exemplary embodiment, dropwise adding the saturated calcium solution to the second mixture may include mixing the saturated calcium solution with the second mixture. In an exemplary embodiment, mixing the saturated calcium solution with the second mixture may include mixing the saturated calcium solution with the second mixture with a volume ratio of the saturated calcium solution to the second mixture between about 15% and about 30%, that is, explicitly define the ratio.

In an exemplary embodiment, forming exemplary polymeric suspension containing calcium-based gel may further include forming the saturated calcium solution by mixing a calcium-containing substance with an acidic alcoholic solution. In an exemplary embodiment, the calcium-containing substance may include at least one of calcium carbonate ($CaCO_3$) and calcium alginate. In an exemplary embodiment, carbon dioxide ($CO_2$) may be produced responsive to mixing the calcium-containing substance with the acidic alcoholic solution. In an exemplary embodiment, the acidic alcoholic solution may be produced by mixing acetic acid with alcohol with a volume ratio of the acetic acid to the alcohol between about 5% and about 20%. In an exemplary embodiment, the saturated calcium solution may include calcium and acetate ions with a concentration between about 5% and about 20% of the saturated calcium solution by weight. In an exemplary embodiment, the alcohol may include at least one of isopropyl alcohol and ethanol.

In an exemplary embodiment, a calcium-based gel 204 may be formed responsive to mixing the saturated calcium solution with the second mixture. In an exemplary embodiment, calcium-based gel 204 may be formed by partial dissolution of calcium acetate particles in the second mixture. In an exemplary embodiment, exemplary polymeric composition may include the calcium acetate particles with a concentration between about 1% and about 4% of exemplary polymeric composition by weight. In an exemplary embodiment, mixing the saturated calcium solution with the second mixture may include mixing the saturated calcium solution with the second mixture using a magnetic stirrer with speed between about 400 rpm and 800 rpm.

In an exemplary embodiment, mixing the saturated calcium solution with the second mixture faster may lead to calcium-based gel 204 with smaller particle size. In an exemplary embodiment, calcium-based gel 204 may include at least one of nanoparticles and microparticles. In an exemplary embodiment, mixing the saturated calcium solution with the second mixture, which contains an alcoholic solution with neutral pH, may lead to the formation of some physical bonds between calcium and the alcohol, which may cause partial dissolution and incomplete precipitation of calcium acetate in the second mixture. As a result, the saturated calcium solution's form may be changed to a gel-like structure in low temperatures.

In an exemplary embodiment, exemplary method 100 may further include converting the suspension formulation to a gel formulation by adding a gelling agent to exemplary polymeric composition in the suspension formulation. In an exemplary embodiment, gelling agent 212 may include a carbomer and a proton acceptor. In the present disclosure, "carbomer" may refer to a series of polymers made from acrylic acid. In an exemplary embodiment, the carbomer may have a concentration between about 0.06 g/ml and about 3 g/ml of exemplary polymeric composition. In an exemplary embodiment, the carbomer may have a concentration of about 0.3 g/ml. In an exemplary embodiment, the carbomer may include polyacrylic acid.

In an exemplary embodiment, the proton acceptor may have a volume ratio between about 0.0001% and about 0.1% of volume of exemplary polymeric composition. In an exemplary embodiment, the proton acceptor may include a trialkanol amine. In an exemplary embodiment, the trialkanol amine may include an alkyl group with a carbon number up to 5. In an exemplary embodiment, the proton acceptor may include triethanolamine (TEA).

Referring again to FIG. 2, exemplary polymeric composition in a suspension formulation 200 and a gel formulation 202 may include a modified solvent phase and a solid phase dispersed within the modified solvent phase. In an exemplary embodiment, the modified solvent phase may include a calcium-based gel 204. In an exemplary embodiment, the solid phase may include a polymeric matrix and a plurality of desiccant particles 206 encompassed by the polymeric matrix.

In an exemplary embodiment, calcium-based gel 204 may include calcium acetate particles partially dissolved in the alcoholic solution. In an exemplary embodiment, calcium-based gel 204 may have a colloid structure. In an exemplary embodiment, the presence of calcium-based gel 204 in exemplary polymeric compositions 200 and 202 may increase the solid phase's suspension in the modified solvent phase of exemplary polymeric compositions 200 and 202. Without bound by any theory, in an exemplary embodiment, calcium-based gel 204 may also be considered as a weak and compatible thickener due to being partially dissolved in the alcoholic solution without decreasing friction.

In an exemplary embodiment, the polymeric matrix may provide a network for trapping plurality of desiccant particles 206 and form a condensed grip-enhancing composition. In an exemplary embodiment, PVAc 210 may interact with magnesium and calcium of plurality of desiccant particles 206 and suspend plurality of desiccant particles 206 in the modified solvent phase. In an exemplary embodiment, thickener 208, particularly the HPMC, may have polymeric chains, which may trap plurality of desiccant particles 206 and suspend them in the modified solvent phase. In an exemplary embodiment, exemplary polymeric composition may have a particle size between about 70 nm and about 400 µm.

In an exemplary embodiment, exemplary polymeric composition in a gel formulation 202 may be used to prevent alcohol evaporation. In an exemplary embodiment, exemplary polymeric composition in a gel formulation 202 may be easier to handle during consumption. In an exemplary embodiment, exemplary polymeric composition in a gel formulation 202 may further include a gelling agent 212. In an exemplary embodiment, exemplary polymeric composition 200 and 202 may further include an additive, such as organic dyes, inorganic dyes, and fragrant substances.

An exemplary polymeric composition may enhance gripping in different activities and sports, such as climbing, gymnastics, yoga, fitness, weightlifting, track and field, and pole vaulting by increasing chalk adhesion to skin without causing any health problems. In an exemplary embodiment, exemplary polymeric composition may be used by pouring exemplary polymeric composition on the target skin or the object's surface and rubbing it until exemplary polymeric composition being dried.

EXAMPLES

Example 1: Production of Exemplary Polymeric Composition for Enhancing Grip

In this example, exemplary polymeric composition, similar to exemplary polymeric composition 200 of FIG. 2, was produced utilizing a process similar to exemplary method 100 as presented in FIG. 1. At first, a first mixture was formed by adding PVAc with a final concentration of about 3 g/ml (about 0.5 grams) and HMPC with a final concentration of about 1 g/ml (0.2 gram) to a container containing 10 ml isopropyl alcohol and mixed until a transparent mixture obtained. The container was placed in a paraffin bath at a temperature of about 80° C. to achieve reflux. The container was also stirred using a magnetic stirrer with a speed of about 600 rpm. A second mixture was then formed by slowly adding magnesium carbonate with a final concentration of about 6 g/ml (1 gram) to the first mixture.

In the next step, a saturated calcium solution was formed by mixing calcium carbonate with a concentration of about 2 g/ml (0.3 gram) with a solution containing glacial acetic acid (0.15 ml) with a concentration of about 96% and isopropyl alcohol (10 ml) using a magnetic stirrer for a time period of about 1 minute in room temperature. During mixing calcium carbonate with the solution, $CO_2$ was produced and evolved from the solution. In the end, exemplary polymeric composition was formed by dropwise adding the saturated calcium solution (about 3 ml) to the second mixture with a volume ratio of the saturated calcium solution to the second mixture about 21% while stirring. After 10 minutes of stirring, exemplary polymeric composition was cooled down from 80° C. to room temperature.

Figure 3A:
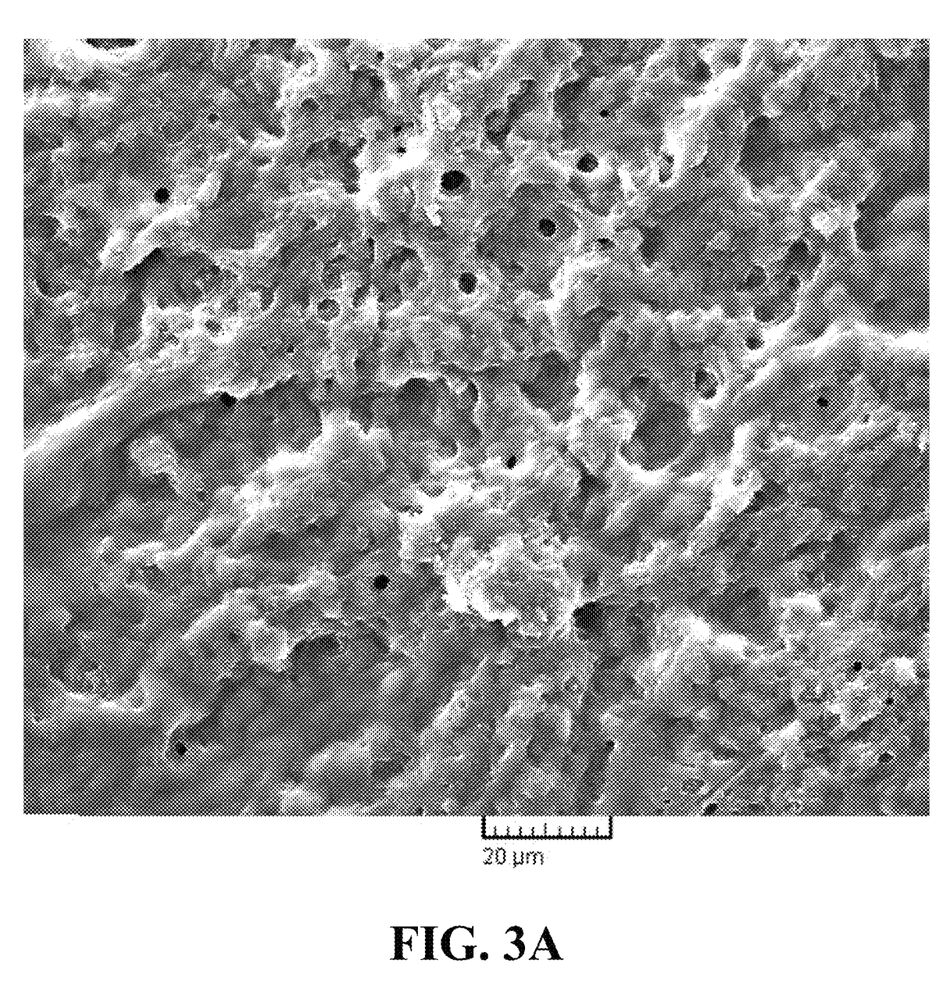
FIG. 3A illustrates a scanning electron microscopy (SEM) image of a polymeric matrix, including polyvinyl acetate (PVAc) and hydroxypropyl methylcellulose (HPMC), consistent with one or more exemplary embodiments of the present disclosure.
Figure 3B:
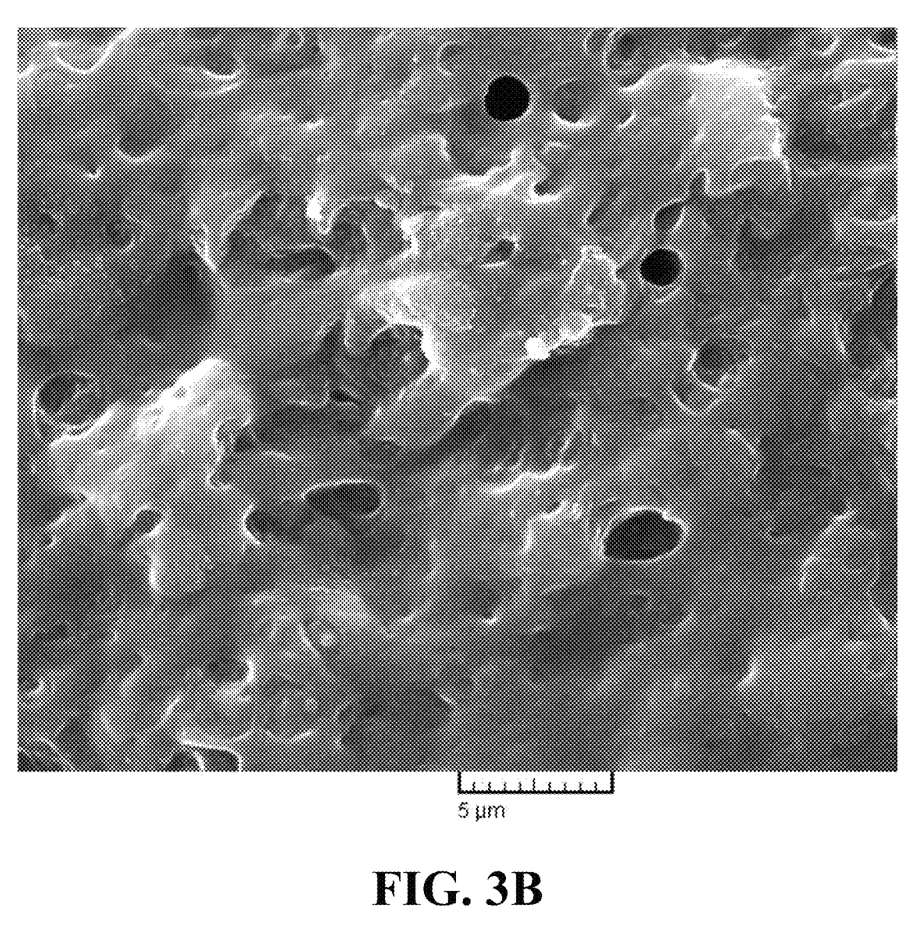
FIG. 3B illustrates a magnified SEM image of the polymeric matrix, including PVAc and HPMC, consistent with one or more exemplary embodiments of the present disclosure.

Example 2: Characterization of Exemplary Polymeric Composition for Enhancing Grip In this example, the physical characterization of exemplary polymeric composition, produced in EXAMPLE 1 using a similar method described in method 100 of FIG. 1, was determined utilizing scanning electron microscopy (SEM) dynamic light scattering (DLS) analysis. FIG. 3A illustrates an SEM image of a polymeric matrix, including the PVAc and the HPMC, consistent with one or more exemplary embodiments of the present disclosure. FIG. 3B illustrates a magnified SEM image of the polymeric matrix, including PVAc and HPMC, consistent with one or more exemplary embodiments of the present disclosure.

Figure 4A:
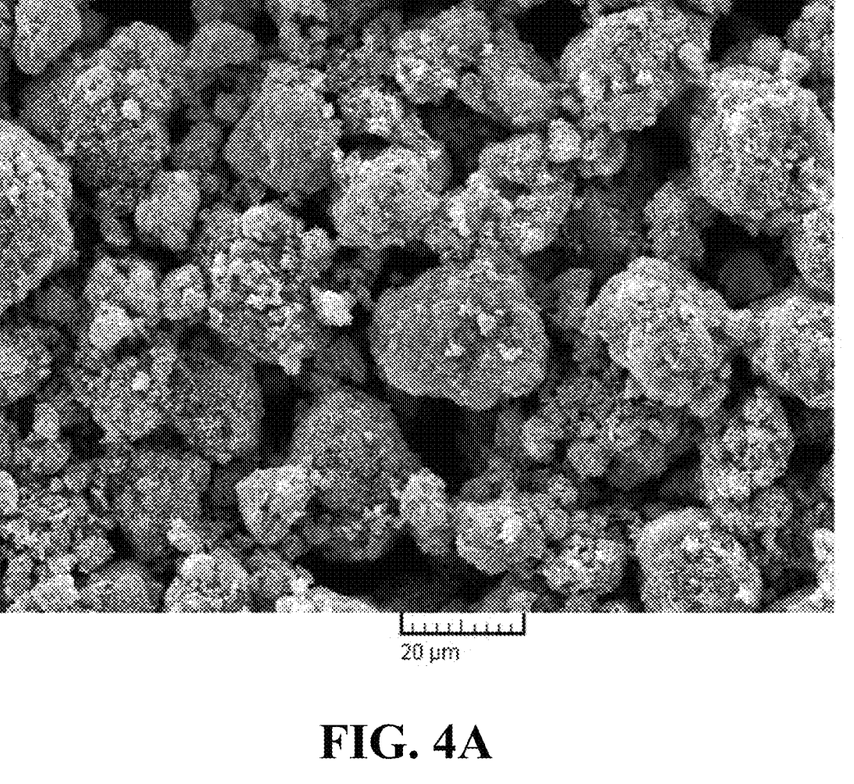
FIG. 4A illustrates an SEM image of an exemplary polymeric composition for enhancing grip, consistent with one or more exemplary embodiments of the present disclosure.
Figure 4B:
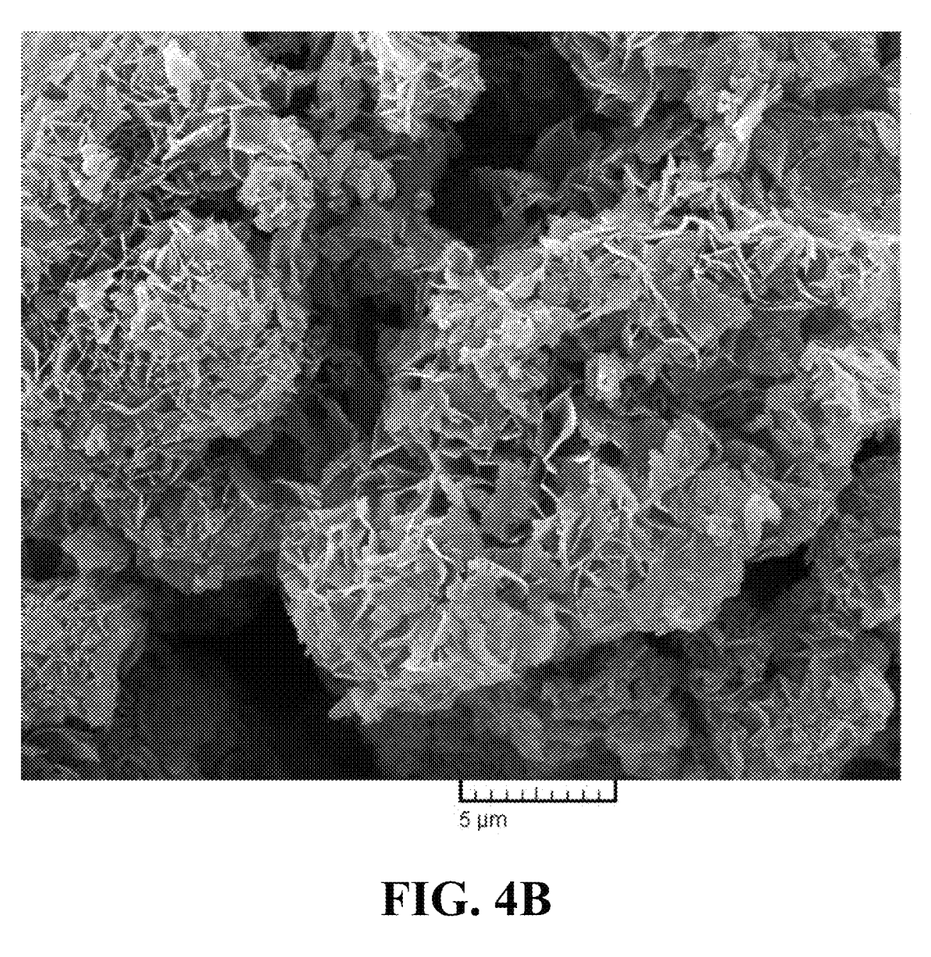
FIG. 4B illustrates a magnified SEM image of an exemplary polymeric composition for enhancing grip, consistent with one or more exemplary embodiments of the present disclosure.

FIG. 4A illustrates an SEM image of an exemplary polymeric composition for enhancing grip, consistent with one or more exemplary embodiments of the present disclosure. FIG. 4B illustrates a magnified SEM image of an exemplary polymeric composition for enhancing grip, consistent with one or more exemplary embodiments of the present disclosure. Referring to FIGS. 3A-3B and FIGS. 4A-4B, comparison between the polymeric matrix FIGS. 3A-3B and exemplary polymeric composition FIGS. 4A-4B indicates the addition of the plurality of desiccant particles to the polymeric matrix had dramatically changed the composition's surface properties after drying. For instance, nano-sheets of the plurality of desiccant particles have decreased smoothness and increased uneven surfaces, which may lead to more friction property.

Figure 5:
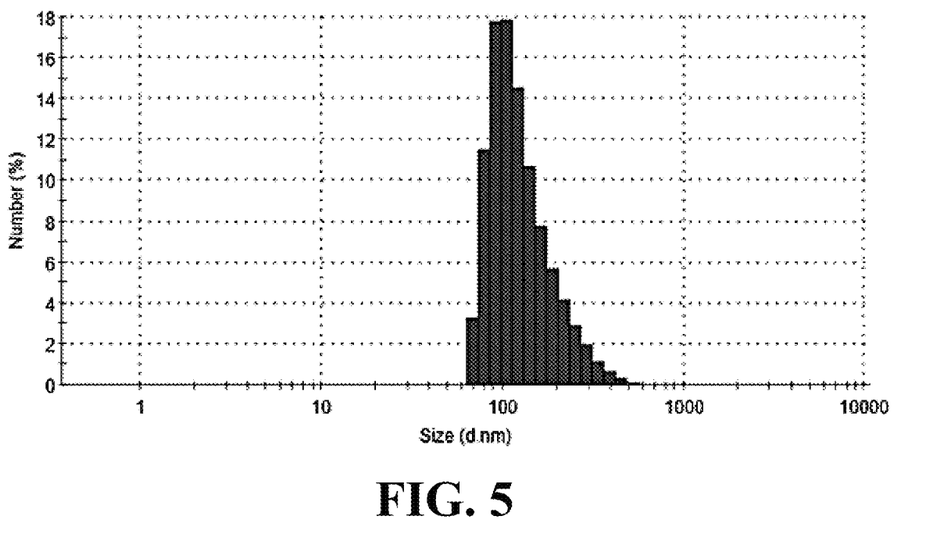
FIG. 5 illustrates a size distribution graph of an exemplary polymeric composition for enhancing grip based on dynamic light scattering (DLS) analysis, consistent with one or more exemplary embodiments of the present disclosure.

FIG. 5 illustrates a size distribution graph of an exemplary polymeric composition for enhancing grip based on DLS analysis, consistent with one or more exemplary embodiments of the present disclosure. Referring to FIG. 5, exemplary polymeric composition containing the polymeric matrix, calcium-based nano-gel, and the plurality of desiccant particles had a particle size between about 70 and about 500 nm with an average size of about 190 nm.

Figure 6:
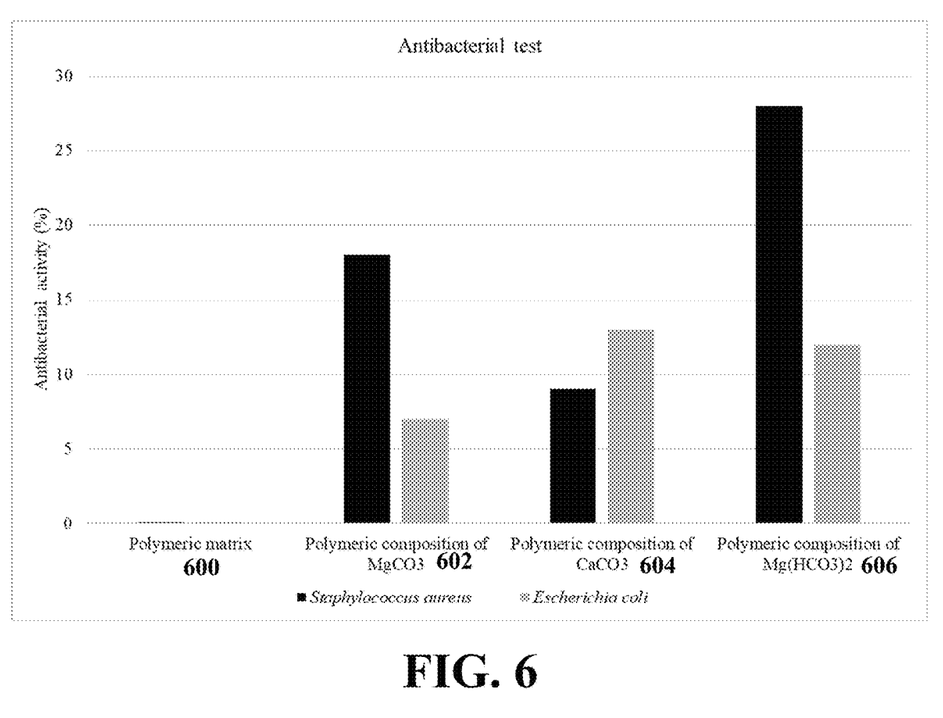
FIG. 6 illustrates the results of an antimicrobial test of exemplary polymeric compositions, consistent with one or more exemplary embodiments of the present disclosure.

Example 3: Antimicrobial Activity of Exemplary Polymeric Composition for Enhancing Grip In this example, the antibacterial properties of exemplary polymeric compositions were assessed using the wall agar diffusion test. FIG. 6 illustrates the results of an antimicrobial test of different compositions, including polymeric matrix (PVAc and HPMC) 600, exemplary polymeric composition of $MgCO_3$ 602, exemplary polymeric composition of $CaCO_3$ 604, and exemplary polymeric composition of $Mg(HCO_3)_2$ 606, consistent with one or more exemplary embodiments of the present disclosure. Referring to FIG. 6, polymeric matrix 600 containing PVAc and HPMC did not show antibacterial activity that may relate to the polymeric matrix's inability to diffuse into the agar gel or degradability of the polymeric matrix.

However, all exemplary polymeric compositions 602, 604, and 606 showed significantly higher antibacterial activity than polymeric matrix 600 against *Staphylococcus aureus* and *Escherichia coli*. Moreover, exemplary polymeric composition of $MgCO_3$ 602 and exemplary polymeric composition of $Mg(HCO_3)_2$ 606 showed higher antibacterial activity against *Staphylococcus aureus* than exemplary polymeric composition of $CaCO_3$ 604. Also, exemplary polymeric composition of $CaCO_3$ 604 and exemplary polymeric composition of $Mg(HCO_3)_2$ 606 showed higher antibacterial activity against *Escherichia coli* than exemplary polymeric composition of $MgCO_3$ 602.

While the foregoing has described what may be considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such away. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure and is not to be interpreted as reflecting an intention that the claimed implementations require more features than are expressly recited in each claim. Rather, as the following claims reflect, the inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in the light of the attached claims and their equivalents. Also, various modifications and changes may be made within the scope of the attached claims.

What is claimed is:

1. A polymeric composition for enhancing grip, comprising:
    a modified solvent phase, comprising:
        calcium-based gel comprising calcium acetate particles partially dissolved in an alcoholic solution; and
    a solid phase dispersed within the modified solvent phase, the solid phase comprising:
        a polymeric matrix, comprising:
            polyvinyl acetate (PVAc) with a concentration between 2 g/ml and 5 g/ml of the polymeric composition; and
            a thickener comprising hydroxypropyl methylcellulose (HPMC); and
        a plurality of desiccant particles encompassed by the polymeric matrix, the plurality of desiccant particles comprising magnesium carbonate.

2. A polymeric composition for enhancing grip, the polymeric composition comprising:
    a modified solvent phase, comprising:
        calcium-based gel comprising calcium acetate particles partially dissolved in an alcoholic solution; and
    a solid phase dispersed within the modified solvent phase, the solid phase comprising:
        a polymeric matrix comprising polyvinyl acetate (PVAc) and a thickener; and
        a plurality of desiccant particles encompassed by the polymeric matrix.

3. The polymeric composition of claim 2, wherein the PVAc has a concentration between 2 g/ml and 5 g/ml of the polymeric composition.

4. The polymeric composition of claim 2, wherein the polymeric composition comprises the calcium acetate particles with a concentration between 1% and 4% of the polymeric composition by weight.

5. The polymeric composition of claim 2, wherein the calcium-based gel comprises at least one of nanoparticles and microparticles.

6. The polymeric composition of claim 2, wherein the alcoholic solution comprises alcohol dissolved in water with a concentration of the alcohol between 60% and 99% by volume, the alcohol comprising at least one of isopropyl alcohol and ethanol.

7. The polymeric composition of claim 6, wherein the alcoholic solution comprises a volume ratio between 60% and 94% of volume of the polymeric composition.

8. The polymeric composition of claim 2, wherein the plurality of desiccant particles comprises at least one of magnesium carbonate ($MgCO_3$), magnesium hydrogen carbonate ($Mg(HCO_3)_2$), calcium carbonate ($CaCO_3$).

9. The polymeric composition of claim 2, wherein the plurality of desiccant particles have a concentration between 3 g/ml and 15 g/ml of the polymeric composition.

10. The polymeric composition of claim 2, wherein the thickener comprises at least one of hydroxypropyl methylcellulose (HPMC), colophony resin (rosin), hydroxypropyl cellulose, styrax benzoin gum, hydroxyl ethyl cellulose, and wax.

11. The polymeric composition of claim 2, wherein the thickener has a concentration between 1 g/ml and 3 g/ml of the polymeric composition.

12. The polymeric composition of claim 2, wherein the polymeric composition has a particle size between 70 nm and 400 µm.

13. The polymeric composition of claim 2, wherein the polymeric composition has a suspension formulation or a gel formulation.

14. The polymeric composition of claim 2 further comprising a gelling agent, the gelling agent comprises a carbomer and a proton acceptor.

15. The polymeric composition of claim 14, wherein the carbomer has a concentration between 0.06 g/ml and 3 g/ml of the polymeric composition.

16. The polymeric composition of claim 15, wherein the carbomer comprises polyacrylic acid.

17. The polymeric composition of claim 14, wherein the proton acceptor has a volume ratio between 0.0001% and 0.1% of volume of the polymeric composition.

18. The polymeric composition of claim 17, wherein the proton acceptor comprises a trialkanol amine, the trialkanol amine comprising an alkyl group with a carbon number up to 5.

19. A method for producing a polymeric composition for enhancing grip, the method comprising:
    forming a first mixture by dissolving polyvinyl acetate (PVAc) and a thickener in an alcoholic solution;
    forming a second mixture by adding a plurality of desiccant particles to the first mixture; and
    producing the polymeric composition containing calcium-based gel by dropwise adding a saturated calcium solution to the second mixture, the saturated calcium solution comprising calcium acetate particles with a concentration between 5% and 20% of the saturated calcium solution by weight.

20. The method of claim 19, wherein dropwise adding the saturated calcium solution to the second mixture comprises mixing the saturated calcium solution with the second mixture with a volume ratio of the saturated calcium solution to the second mixture between 15% and 30%.

* * * * *